United States Patent
Harjes et al.

(12)

(10) Patent No.: US 11,684,769 B2
(45) Date of Patent: Jun. 27, 2023

(54) IMPLANTABLE BLOOD PUMP ASSEMBLY INCLUDING PRESSURE SENSOR AND METHODS OF ASSEMBLING SAME

(71) Applicant: TC1 LLC, St. Paul, MN (US)

(72) Inventors: Daniel I. Harjes, Carlisle, MA (US); Eric Lee, Oakland, CA (US); Jin Woo Park, Suwanee, GA (US)

(73) Assignee: TC1 LLC, St. Paul, MN (US)

( * ) Notice: Subject to any disclaimer, the term of this patent is extended or adjusted under 35 U.S.C. 154(b) by 480 days.

(21) Appl. No.: 16/721,432

(22) Filed: Dec. 19, 2019

(65) Prior Publication Data

US 2020/0197586 A1 Jun. 25, 2020

Related U.S. Application Data

(60) Provisional application No. 62/783,950, filed on Dec. 21, 2018.

(51) Int. Cl.
 *A61M 60/419* (2021.01)
 *A61M 60/148* (2021.01)
 (Continued)

(52) U.S. Cl.
 CPC ........ *A61M 60/419* (2021.01); *A61M 60/148* (2021.01); *A61M 60/178* (2021.01);
 (Continued)

(58) Field of Classification Search
 CPC .............. A61M 60/419; A61M 60/148; A61M 205/0294; A61M 205/103; A61M 205/3344; A61M 205/3365; A61M 206/20
 See application file for complete search history.

(56) References Cited

U.S. PATENT DOCUMENTS 3,911,897 A 10/1975 Leachman, Jr.
4,944,748 A 7/1990 Bramm et al.
(Continued)

FOREIGN PATENT DOCUMENTS

EP 3181163 A1 6/2017

OTHER PUBLICATIONS

International Search Report and Written Opinion for International Patent Application No. PCT/US2019/067496, dated Jul. 7, 2020, 20 pages.

*Primary Examiner* — Catherine M Voorhees
*Assistant Examiner* — Roland Dinga
(74) *Attorney, Agent, or Firm* — Armstrong Teasdale LLP

(57) ABSTRACT

Disclosed herein is an implantable blood pump assembly that includes a housing defining an inlet, an outlet, a flow path extending from the inlet to the outlet, and an internal compartment separated from the flow path. The blood pump assembly further includes a rotor positioned within the flow path and operable to pump blood from the inlet to the outlet, a stator positioned within the internal compartment and operable to drive the rotor, and an inlet conduit connected to the housing inlet and having a downstream end that has a reduced cross-sectional area that produces a localized region of high velocity blood flow. The blood pump assembly further includes at least one pressure sensor positioned between the inlet and the outlet and configured to detect a pressure of blood flowing through the flow path. The pressure sensor is located adjacent the downstream end of the inlet conduit.

18 Claims, 7 Drawing Sheets

(51) Int. Cl.
*A61M 60/816* (2021.01)
*A61M 60/814* (2021.01)
*A61M 60/538* (2021.01)
*A61M 60/531* (2021.01)
*A61M 60/422* (2021.01)
*A61M 60/178* (2021.01)
*A61M 60/232* (2021.01)

(52) U.S. Cl.
CPC ........ *A61M 60/232* (2021.01); *A61M 60/422* (2021.01); *A61M 60/531* (2021.01); *A61M 60/538* (2021.01); *A61M 60/814* (2021.01); *A61M 60/816* (2021.01); *A61M 2205/0294* (2013.01); *A61M 2205/103* (2013.01); *A61M 2205/3344* (2013.01); *A61M 2205/3365* (2013.01); *A61M 2206/20* (2013.01)

(56) References Cited

U.S. PATENT DOCUMENTS

| | | |
|---|---|---|
| 6,176,822 B1 * | 1/2001 | Nix ..................... A61M 60/419 623/3.1 |
| 6,623,420 B2 | 9/2003 | Reich et al. |
| 7,850,594 B2 | 12/2010 | Sutton et al. |
| 8,096,935 B2 | 1/2012 | Sutton et al. |
| 8,177,838 B2 | 5/2012 | Vodermayer et al. |
| 8,449,444 B2 | 5/2013 | Poirier |
| 8,506,471 B2 | 8/2013 | Bourque |
| 9,125,977 B2 | 9/2015 | Nishimura et al. |
| 9,713,663 B2 | 7/2017 | Medvedev et al. |
| 9,849,224 B2 | 12/2017 | Angwin et al. |
| 10,010,662 B2 | 7/2018 | Wiesener et al. |
| 2003/0045772 A1 | 3/2003 | Reich et al. |
| 2005/0107658 A1 * | 5/2005 | Brockway ............. A61M 60/50 600/16 |
| 2008/0077068 A1 * | 3/2008 | Orr ..................... A61M 1/3667 604/6.11 |
| 2010/0121133 A1 | 5/2010 | Schumer |
| 2010/0222635 A1 | 9/2010 | Poirier |
| 2010/0222878 A1 | 9/2010 | Poirier |
| 2014/0073837 A1 | 3/2014 | Kerkhoffs et al. |
| 2015/0141842 A1 * | 5/2015 | Spanier ............... A61B 5/02154 600/478 |
| 2015/0290375 A1 * | 10/2015 | Angwin .............. A61M 60/148 600/16 |
| 2016/0325034 A1 | 11/2016 | Wiktor et al. |
| 2016/0375187 A1 | 12/2016 | Lee et al. |
| 2017/0128646 A1 | 5/2017 | Karch |
| 2017/0157309 A1 * | 6/2017 | Begg ..................... F04D 29/242 |

* cited by examiner

IMPLANTABLE BLOOD PUMP ASSEMBLY INCLUDING PRESSURE SENSOR AND METHODS OF ASSEMBLING SAME

CROSS-REFERENCE TO RELATED APPLICATIONS

This application claims priority to U.S. Provisional Patent Application Ser. No. 62/783,950, filed on Dec. 21, 2018, the disclosure of which is hereby incorporated by reference in its entirety.

BACKGROUND OF THE DISCLOSURE a. Field of the Disclosure

The present disclosure relates generally to mechanical circulatory support systems, and more specifically relates to implantable blood pump assemblies that include one or more pressure sensors for detecting a blood pressure within the ventricle of a patient's heart.

b. Background

Ventricular assist devices, known as VADs, are implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

A controller can be used to control operation of the implanted VAD. The controller can be operatively connected to the VAD via a wired, wireless, and/or mechanical connection, which can be used to supply the VAD with operating power (e.g., electrical and/or mechanical power) and control signals to control the operation of the VAD.

At least some VADs utilize pressure feedback from one or more pressure sensors to control operation of the VAD. Some VADs, for example, use a pressure sensor located in the left ventricle of a patient's heart to measure pressure and monitor a patient's cardiac cycle for control of the VAD. Other VADs include a pressure sensor connected to or located within a fluid conduit that connects the VAD to a patient's heart, such as an inflow or outflow conduit.

The location of pressure sensors used in previous VADs has several drawbacks that have prevented wide-spread adoption. For example, implanting a pressure sensor in the ventricle of a patient's heart requires separate steps or procedures from the VAD implant procedure, and also requires separate power lines and/or communication pathways to be run between the pressure sensor and the VAD, increasing the burden of surgical placement. Additionally, pressure sensors located within the ventricle of a patient's heart or within a fluid conduit can be susceptible to tissue overgrowth that can cause sensor drift and/or accuracy deficiencies. Further, pressure sensors located within the ventricle of a patient's heart or within a fluid conduit can lack sufficient mechanical stability, making the pressure sensors susceptible to positional drift, mechanical strain, and resulting measurement inaccuracies.

Accordingly, a need exists for improved VADs that use pressure sensors to monitor a patient's cardiac cycle and/or control operation of the VAD.

SUMMARY OF THE DISCLOSURE

The present disclosure is directed to an implantable blood pump assembly that includes a housing defining an inlet, an outlet, a flow path extending from the inlet to the outlet, and an internal compartment separated from the flow path. The blood pump assembly further includes a rotor positioned within the flow path and operable to pump blood from the inlet to the outlet, a stator positioned within the internal compartment and operable to drive the rotor, and an inlet conduit connected to the housing inlet and having a downstream end that has a reduced cross-sectional area that produces a localized region of high velocity blood flow. The blood pump assembly further includes at least one pressure sensor positioned between the inlet and the outlet and configured to detect a pressure of blood flowing through the flow path. The pressure sensor is located adjacent the downstream end of the inlet conduit.

The present disclosure is further directed to a circulatory support system that includes an implantable blood pump and a controller. The implantable blood pump includes a housing that defines an inlet, an outlet, a flow path extending from the inlet to the outlet, and an internal compartment separated from the flow path. The implantable blood pump further includes a rotor positioned within the flow path and operable to pump blood from the inlet to the outlet, a stator positioned within the internal compartment and operable to drive the rotor, and at least one pressure sensor positioned between the inlet and the outlet and configured to detect a pressure of blood flowing through the flow path. The controller is operatively connected to the at least one pressure sensor and the stator, and is positioned within the internal compartment. The controller is configured to control a rotational speed of the rotor based on the pressure detected by the at least one pressure sensor.

The present disclosure is further directed to a method of assembling a blood pump assembly. The method includes providing a blood pump housing that defines an inlet, an outlet, a flow path extending from the inlet to the outlet, and an internal compartment, positioning a rotor within the flow path such that the rotor is operable to pump blood from the inlet to the outlet, positioning a stator within the internal compartment such that the stator is operable to drive the rotor, and connecting a downstream end of an inlet conduit to the housing inlet. The downstream end of the inlet conduit has a reduced cross-sectional area that produces a localized region of high velocity blood flow. The method further includes positioning at least one pressure sensor between the inlet and the outlet, and adjacent to the downstream end of the inlet conduit such that the at least one pressure sensor is configured to detect a pressure of blood flowing through the flow path.

DETAILED DESCRIPTION OF THE DISCLOSURE

The present disclosure is directed to implantable blood pump assemblies that include one or more pressure sensors for detecting a blood pressure within a ventricle of a patient's heart. Embodiments of the implantable blood pump assemblies disclosed herein include one or more pressure sensors located on or within a housing of the blood pump assembly and/or adjacent to or within a localized region of high velocity blood flow. The position of the pressure sensors in the implantable blood pump assemblies disclosed herein facilitates improved blood pressure measurements. For example, by locating pressure sensors adjacent to or within a localized region of high velocity blood flow, tissue overgrowth on the pressure sensors is minimized or reduced. Additionally, pressure sensors that are located within or on the housing of a blood pump assembly can be physically protected by the pump housing and can be securely connected to the pump housing, which reduces or limits positional drift and mechanical stress variations on the pressure sensors.

Further, pressure sensors that are located within or on the housing of a blood pump assembly can be directly connected to an on-board controller of the blood pump assembly for receiving electrical power directly from the controller and for sending pressure measurement signals directly to the controller. Such a direct connection between the pressure sensor and the controller simplifies the implant procedure by eliminating the need to run separate power or communication lines to the pressure sensor, and also improves performance of the blood pump by reducing signal noise in pressure measurements.

Figure 1:
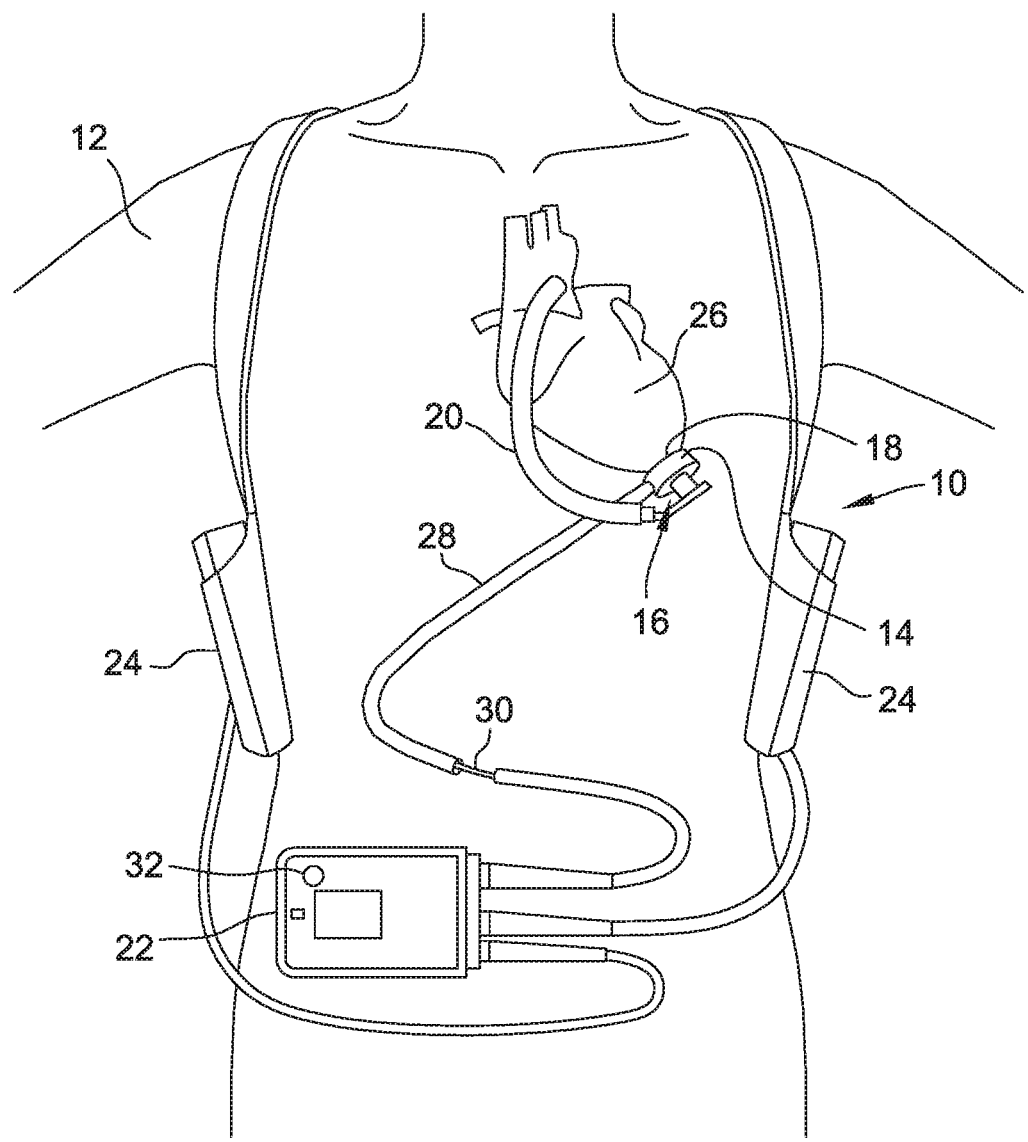
FIG. 1 is an illustration of a mechanical circulatory support system implanted in a patient's body.

Referring now to the drawings, FIG. 1 is an illustration of a mechanical circulatory support system 10 implanted in a patient's body 12. The mechanical circulatory support system 10 includes an implantable blood pump assembly 14 that includes a blood pump 16, a ventricular cuff 18, and an outflow cannula 20. The mechanical circulatory support system 10 also includes an external system controller 22 and one or more power sources 24.

The blood pump assembly 14 can be implemented as or can include a ventricular assist device (VAD) that is attached to an apex of the left ventricle, as illustrated, or the right ventricle, or both ventricles of the heart 26. The blood pump assembly 14 can be attached to the heart 26 via the ventricular cuff 18 which is sewn to the heart 26 and coupled to the blood pump assembly 14. The other end of the blood pump assembly 14 connects to the ascending or descending aorta via the outflow cannula 20 so that the blood pump assembly 14 effectively diverts blood from the weakened ventricle and propels it to the aorta for circulation to the rest of the patient's vascular system. The VAD can include a centrifugal (as shown) or axial flow pump as described in further detail herein that is capable of pumping the entire output delivered to the left ventricle from the pulmonary circulation (i.e., up to 10 liters per minute).

FIG. 1 illustrates the mechanical circulatory support system 10 during battery powered operation. A communication line 28 connects the implanted blood pump assembly 14 to the external system controller 22, which monitors system 10 operation. In the illustrated embodiment, the communication line 28 is shown as a driveline that exits through the patient's abdomen 30, although it should be understood that the blood pump assembly 14 may be connected to the external system controller 22 via any suitable communication line, including wired and/or wireless communication. The system can be powered by either one, two, or more batteries 24. It will be appreciated that although the system controller 22 and power source 24 are illustrated outside/external to the patient body, the communication line 28, system controller 22 and/or power source 24 can be partially or fully implantable within the patient, as separate components or integrated with the blood pump assembly 14.

Figure 2:
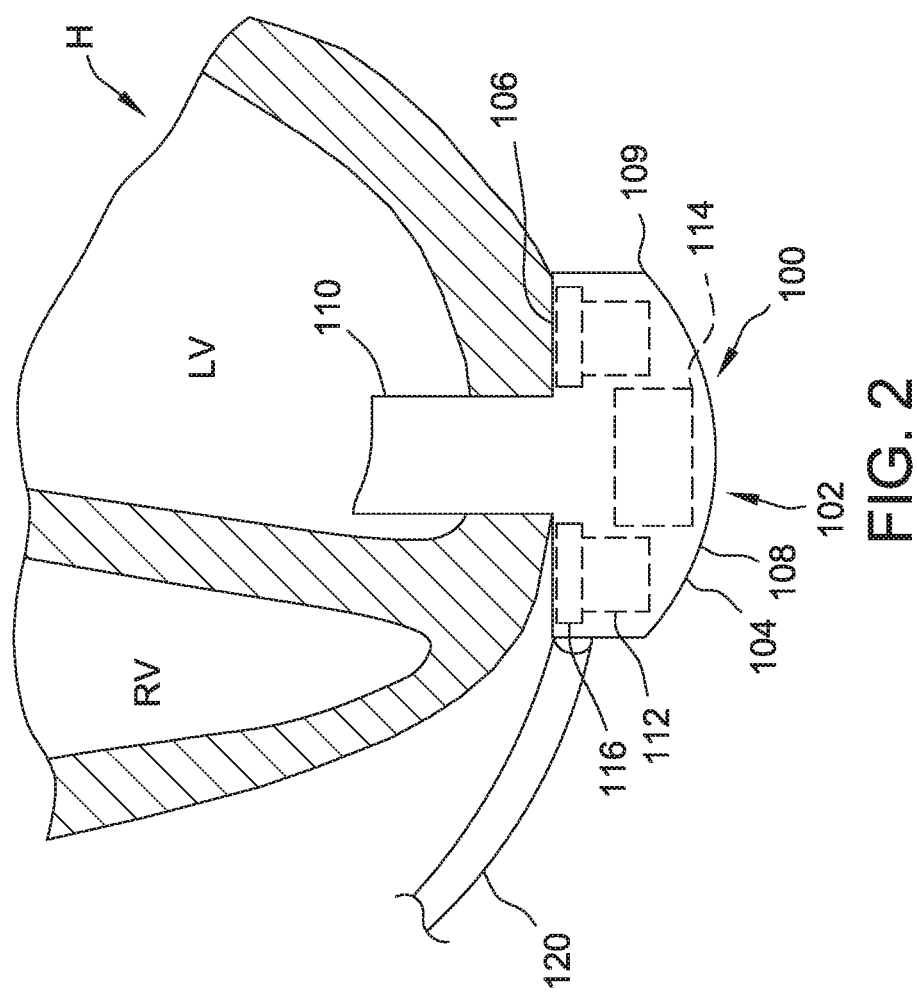
FIG. 2 is an illustration of a blood pump assembly suitable for use in the mechanical circulatory support system of FIG. 1, the blood pump assembly shown in an operational position implanted in a patient's body.
Figure 3:
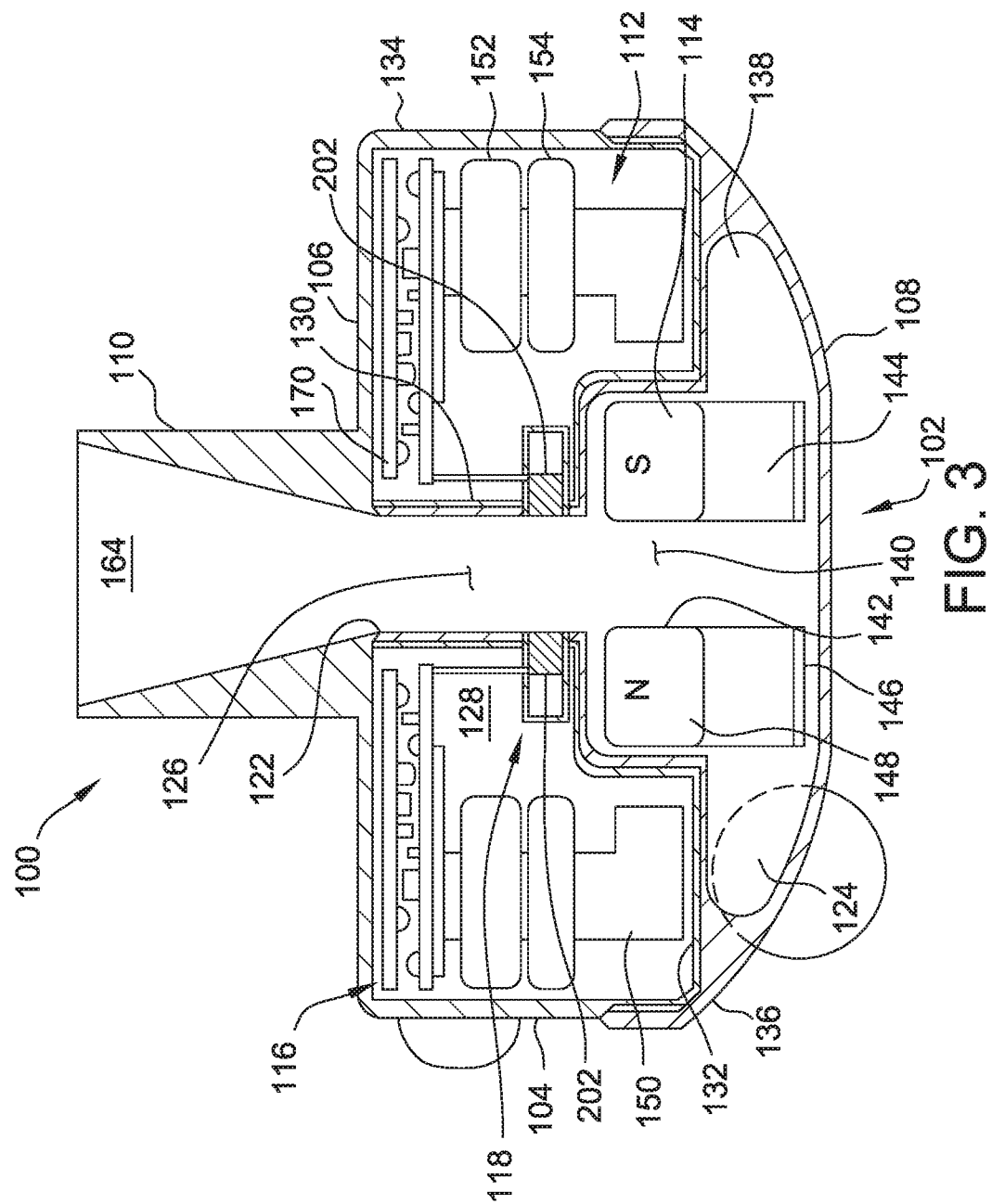
FIG. 3 is a schematic cross-sectional view of the blood pump assembly of FIG. 2.

FIG. 2 is an illustration of an implantable blood pump assembly 100 suitable for use in the mechanical circulatory support system 10 of FIG. 1, where the blood pump assembly 100 is shown in an operational position implanted in a patient's body. FIG. 3 is a schematic cross-sectional view of the blood pump assembly 100 of FIG. 2. In the illustrated embodiment, the blood pump assembly 100 is a left ventricular assist blood pump assembly connected to the left ventricle LV of the heart H.

The blood pump assembly 100 includes a blood pump 102 including a circular shaped housing 104 having a first outer face or wall 106 and a second outer face or wall 108. The blood pump assembly 100 further includes an inlet cannula 110 (generally, an inlet conduit) that, in the illustrated embodiment, extends from the first outer wall 106 of the pump housing 104. When the blood pump assembly 100 is implanted into a patient's body, as shown in FIG. 2, the first outer wall 106 of the housing 104 is positioned against the patient's heart H, and the second outer wall 108 of the housing 104 faces away from the heart H. The inlet cannula 110 extends into the left ventricle LV of the heart H to connect the blood pump assembly 100 to the heart H. The second outer wall 108 of the housing 104 has a chamfered edge 109 to avoid irritating other tissue that may come into contact with the blood pump assembly 100, such as the patient's diaphragm.

The blood pump assembly 100 further includes a stator 112, a rotor 114, an on-board controller 116, and a pressure sensor assembly 118 (FIG. 3), all of which are enclosed within the pump housing 104. In the illustrated embodiment, the stator 112 and the on-board controller 116 are positioned on the inflow side of the pump housing 104 toward the first outer wall 106, and the rotor 114 is positioned along the second outer wall 108. In other embodiments, the stator 112, the rotor 114, and the on-board controller 116 may be positioned at any suitable location within the pump housing 104 that enables the blood pump assembly 100 to function as described herein. Power is supplied to operational components of the blood pump assembly 100 (e.g., the stator 112 and the on-board controller 116) from a remote power supply via a power supply cable 120.

With additional reference to FIG. 3, the pump housing 104 defines an inlet 122 for receiving blood from a ventricle of a heart (e.g., left ventricle LV), an outlet 124 for returning blood to a circulatory system, and a flow path 126 extending from the inlet 122 to the outlet 124. The pump housing 104 further defines an internal compartment 128 separated from the flow path 126, for example, by one or more dividing walls 130.

The pump housing 104 also includes an intermediate wall 132 located between the first outer wall 106 and the second outer wall 108, and a peripheral wall 134 that extends between the first outer wall 106 and the intermediate wall 132. Together, the first outer wall 106, the dividing wall 130, the intermediate wall 132, and the peripheral wall 134 define the internal compartment 128 in which the stator 112 and the on-board controller 116 are enclosed.

In the illustrated embodiment, the pump housing 104 also includes a cap 136 removably attached to the pump housing 104 along the intermediate wall 132. The cap 136 is threadably connected to the pump housing 104 in the illustrated embodiment, although in other embodiments the cap 136 may be connected to the pump housing 104 using any suitable connection means that enables the blood pump assembly 100 to function as described herein. In some embodiments, for example, the cap 136 is non-removably connected to the pump housing 104, for example, by welding. The removable cap 136 includes the second outer wall 108, the chamfered edge 109, and defines the outlet 124. The cap 136 also defines a volute 138 that is in fluid communication with the outlet 124, and a rotor chamber 140 in which the rotor 114 is positioned. The cap 136 can be attached to the pump housing 104 using any suitable connection structure. For example, the cap 136 can be engaged via threads with the peripheral wall 134 to seal the cap 136 in engagement with the peripheral wall 134.

The rotor 114 is positioned within the blood flow path 126, specifically, within the rotor chamber 140, and is operable to rotate in response to an electromagnetic field generated by the stator 112 to pump blood from the inlet 122 to the outlet 124. The rotor defines a central aperture 142 through which blood flows during operation of the blood pump 102. The rotor 114 includes impeller blades 144 located within the volute 138 of the blood flow path 126, and a shroud 146 that covers the ends of the impeller blades 144 facing the second outer wall 108 to assist in directing blood flow into the volute 138.

In the illustrated embodiment, the rotor 114 includes a permanent magnet 148 that defines the central aperture 142. The permanent magnet 148 has a permanent magnetic north pole N and a permanent magnetic south pole S for combined active and passive magnetic levitation of the rotor 114 and for rotation of the rotor 114. In operation, the stator 112 is controlled to drive (i.e., rotate) the rotor and to radially levitate the rotor 114 by generating electromagnetic fields that interact with the permanent magnetic poles S and N of the permanent magnet 148.

Any suitable stator 112 can be employed to rotate the rotor 114. The stator 112 generally includes a plurality of winding structures that generate suitable electromagnetic fields that interact with the rotor 114 to cause rotor 114 to rotate and levitate. In the illustrated embodiment, the stator 112 includes a plurality of pole pieces 150 arranged circumferentially at intervals around the dividing wall 130. The example blood pump assembly 100 includes six pole pieces 150, two of which are visible in FIG. 3. In other embodiments, the blood pump assembly 100 can include more than or less than six pole pieces, such as four pole pieces, eight pole pieces, or any other suitable number of pole pieces that enables the blood pump assembly 100 to function as described herein. In the illustrated embodiment, each of the pole pieces 150 includes a drive coil 152 for generating an electromagnetic field to rotate the rotor 114, and a levitation coil 154 for generating an electromagnetic field to control the radial position of the rotor 114.

Each of the drive coils 152 and the levitation coils 154 includes multiple windings of a conductor wound around the pole pieces 150. The drive coils 152 and the levitation coils 154 of the stator 112 are arranged in opposing pairs and are controlled to drive the rotor and to radially levitate the rotor 114 by generating electromagnetic fields that interact with the permanent magnetic poles S and N of the permanent magnet 148. Suitable methods for generating electromagnetic fields to rotate and radially levitate the rotor 114 are described, for example, in U.S. Pat. No. 9,849,224, the entire contents of which are incorporated herein by reference for all purposes. Although the drive coil 152 and levitation coil 154 are shown as separate coils in the illustrated embodiment, it should be understood that the drive coil 152 and levitation coil 154 may be implemented as a single coil configured to generate electromagnetic fields for both rotating and radially levitating the rotor 114.

Figure 4:
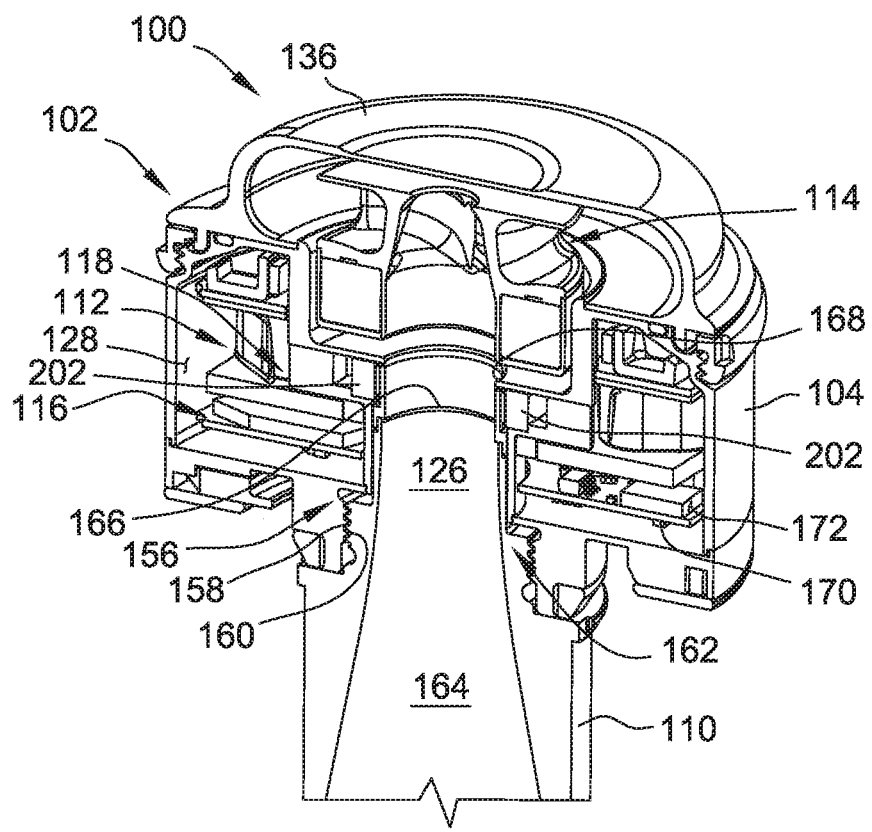
FIG. 4 is a perspective cut away view of the blood pump assembly of FIG. 2.

The inlet cannula 110 is attached to the pump housing 104 at the inlet 122. As shown in FIG. 4, the pump housing 104 includes an inlet cannula receiving portion 156 that includes suitable connecting structure for connecting the inlet cannula 110 to the pump housing 104. In the illustrated embodiment, the pump housing 104 includes an internally threaded sleeve 158 that threadably engages external threads 160 on a downstream end 162 of the inlet cannula 110 to connect the inlet cannula 110 to the pump housing 104.

The inlet cannula 110 defines an inlet flow path 164 that supplies blood to the inlet 122 of the pump housing 104. As shown in FIG. 4, in the illustrated embodiment, the inlet cannula 110 extends into the blood flow path 126 defined by the pump housing 104 such that the inlet flow path 164 partially overlaps with the blood flow path 126.

The downstream end 162 of the inlet cannula 110 has a reduced cross-sectional area (e.g., relative to an upstream end of the inlet cannula 110) that produces a localized region of high velocity blood flow through the inlet flow path 164 and the blood flow path 126. Specifically, the cross-sectional area of the inlet flow path 164 gradually and continuously decreases towards the downstream end 162 of the inlet cannula 110 such that blood flowing through the inlet cannula 110 at a constant flow rate will experience an increase in velocity as it flows through the downstream end 162 of the inlet cannula 110. Consequently, during operation of the blood pump assembly 100, the reduced-cross-sectional area of the downstream end 162 produces a localized region of high velocity blood flow that flows through the inlet 122 and through the blood flow path 126.

The pressure sensor assembly 118 includes one or more pressure sensors 202 configured to detect a pressure of blood flowing through the blood flow path 126. In the illustrated embodiment, the pressure sensor assembly 118 includes two pressure sensors 202, although the pressure sensor assembly 118 can include more than or less than two pressure sensors 202 in other embodiments. The pressure sensors 202 are located adjacent the downstream end 162 of the inlet cannula 110, at the interface between the inlet cannula 110 and the pump housing 104. More specifically, the pressure sensors 202 are located between an outlet 166 of the inlet cannula 110 and an inlet 168 to the rotor chamber 140.

Figure 5:
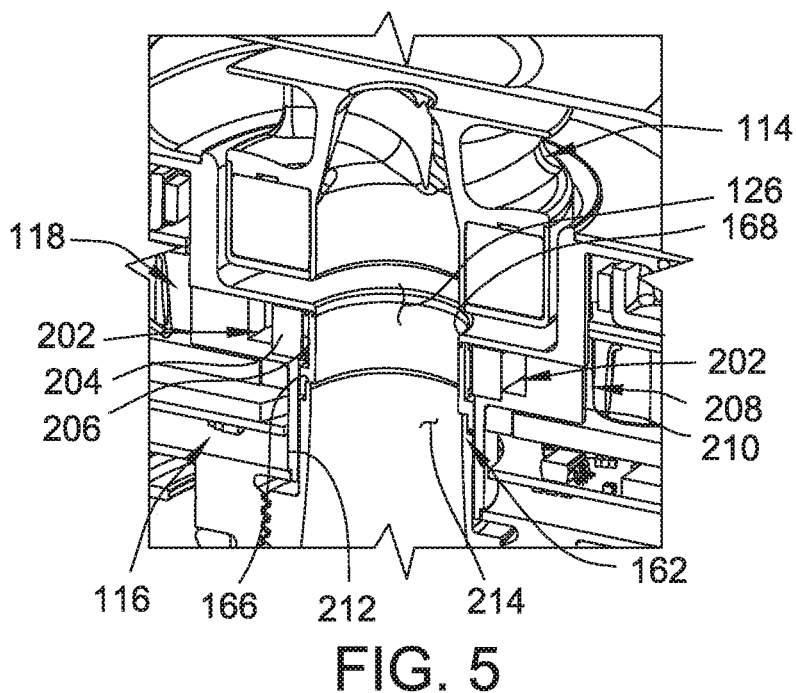
FIG. 5 is an enlarged view of the blood pump assembly of FIG. 4.
Figure 6:
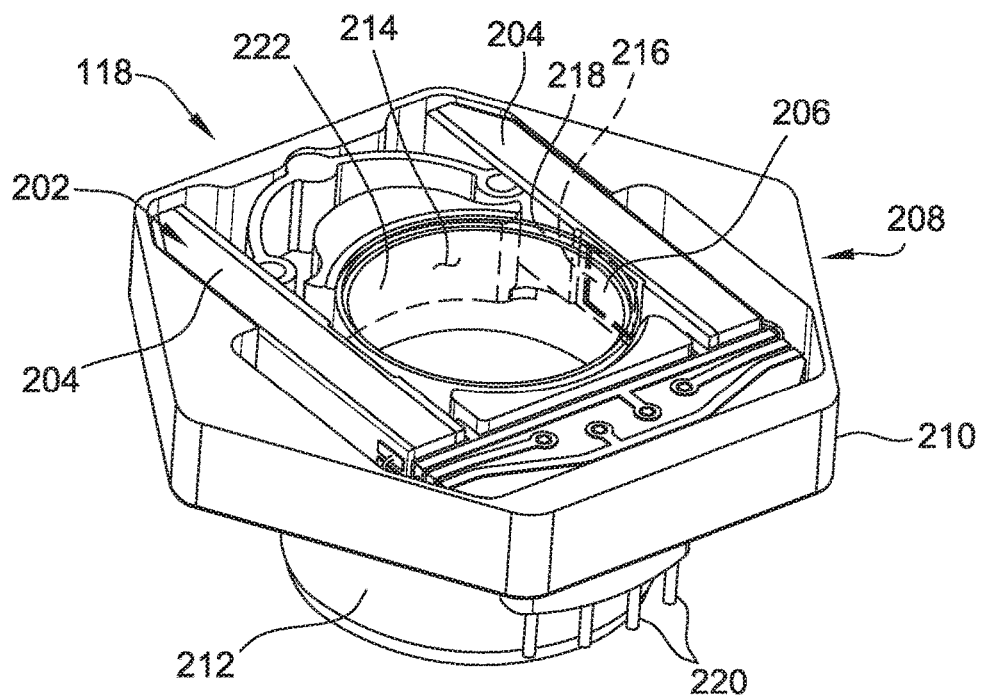
FIG. 6 is a perspective view of a sensor assembly included in the blood pump assembly of FIG. 4.

As shown in FIGS. 5 and 6, in the illustrated embodiment, each pressure sensor 202 includes a sensing element 204 and a deflectable membrane 206 positioned between the sensing element 204 and the blood flow path 126. Pressure sensing elements suitable for use in the pressure sensors 202 include, for example and without limitation, capacitive pressure sensing elements and piezo-resistive pressure sensing elements. Suitable materials from which the deflectable membrane 206 can be constructed include, for example and without limitation, glass.

In the illustrated embodiment, the pressure sensor assembly 118 includes a housing 208 that includes an enclosure 210 and a sleeve 212 extending upstream from the enclosure 210. The pressure sensors 202 are connected to the sensor assembly housing 208 and are positioned within the sensor assembly housing 208 (specifically, within the enclosure 210) diametrically opposite one another. The sleeve 212 receives the downstream end 162 of the inlet cannula 110 such that the downstream end 162 of the inlet cannula 110 is positioned within the sleeve 212 when the blood pump assembly 100 is assembled. Further, in this embodiment, the sleeve 212 defines the dividing wall 130 (FIG. 3) of the pump housing 104.

The sensor assembly housing 208 (specifically, the enclosure 210 and the sleeve 212) defines a flow path 214 that is concentric with the downstream end 162 of the inlet cannula 110 and the blood flow path 126 when the blood pump assembly 100 is assembled. The enclosure 210 of the sensor assembly housing 208 has two windows 216 (FIG. 6) defined therein along a radial inner surface 218 of the enclosure 210. Each of the windows 216 is defined in the enclosure 210 at a location that corresponds to the location of one of the pressure sensors 202 such that each of the pressure sensors 202 can detect the pressure of fluid flow through the flow path 214 and the blood flow path 126 via the windows 216.

The sensor assembly housing 208 further includes a flexible annular membrane 222 positioned within the flow path 214 along the radial inner surface 218. The flexible membrane 222 covers or occludes windows 216, and provides a smooth, inner surface along the flow path 214 to prevent or inhibit turbulent blood flow. The pressure of fluid flowing through the flow path 214 is transmitted to pressure sensors 202 through the flexible membrane 222. Suitable materials from which the flexible membrane 222 can be constructed include, for example and without limitation, soft polymeric materials, such as silicone.

The pressure sensors 202 are connected to the on-board controller 116 by suitable electrical conduits for receiving electrical power therefrom and sending pressure measurement signals thereto. In the illustrated embodiment, each of the pressure sensors 202 is directly connected to the on-board controller 116 by a plurality of pin connectors 220 that extend from one of the pressure sensors 202, out of the enclosure 210, and to the on-board controller 116. In other words, each of the pressure sensors 202 is connected to the on-board controller 116 via a suitable electrical conduit without intervening controllers, signal processing components, or similar equipment. The pressure sensors 202 are connected to the on-board controller 116 by four pin connectors 220 in the illustrated embodiment. In other embodiments, the pressure sensors 202 can be connected to the on-board controller 116 by more than or less than four pin-connectors.

In some embodiments, a portion 172 of the internal compartment 128 (shown in FIG. 4) is hermetically sealed from the internal cavity defined by the enclosure 210 to inhibit fluid (e.g., blood) ingress into the portion of the internal compartment 128 in which electronics (e.g., stator 112 and on-board controller 116) are housed. In the illustrated embodiment, for example, the sensor assembly housing 208 forms a seal against the pump housing 104 to hermetically seal the portion 172 of the internal compartment 128 (shown in FIG. 4) in which electronics are housed from the internal cavity defined by the enclosure 210.

The location of pressure sensors 202 facilitates accurate measurement of pressure within the left ventricle of the heart. For example, by locating the pressure sensors 202 adjacent the downstream end 162 of the inlet cannula 110, which is connected to the left ventricle, the pressure detected by the pressure sensors 202 within the blood flow path 126 provides an accurate pressure measurement for determining the pressure within the left ventricle of the heart. The pressure measurements detected by the pressure sensors 202 can be used to determine the pressure waveform of the left ventricle (i.e., pressure in the left ventricle over time), which, in turn, can be used to identify a number of clinically relevant cardiac events or characteristics. For example, the pressure waveform of the left ventricle can be used to determine the left ventricular filling pressure, or preload (Frank-Starling), which is a primary physiologic mechanism to regulate cardiac output. Increasing left ventricular preload causes an increase in stroke volume and stretch-dependent contractility. As described further herein, the left ventricular pressure waveform can also be used to identify heart rate, left ventricular contractility (i.e., maximum systolic dP/dt), end-systolic left ventricular pressure, end-diastolic left ventricular pressure, atrial kick pressure, maximum left ventricular filling pressure, average left ventricular filling pressure, left ventricular relaxation (i.e., minimum systolic dP/dt), and valve openings and closures. The same cardiac events or characteristics can be determined for the right ventricle in right ventricle assist devices or bi-ventricle assist devices. In some embodiments, a correction factor is applied to the pressure measured by the pressure sensors 202 (e.g., using on-board controller 116) to assess true ventricle pressure. The correction factor may account for "nozzle" effects due to fluid accelerating as the cross-section changes in the inlet cannula 110. The correction factor can be based, for example, on flow (estimated using the rotor drive current) and Bernoulli's equation, and additional terms (e.g., experimentally determined coefficients) based on known fluid dynamic principles and equations.

The location of the pressure sensors 202 facilitates measuring left ventricular pressure with improved accuracy. For example, previous ventricular assist devices included pressure sensors at locations that were susceptible to tissue overgrowth that resulted in sensor drift and/or accuracy deficiencies. By locating pressure sensors 202 adjacent the downstream end 162 of the inlet cannula 110, the pressure sensors 202 are located adjacent the localized region of high velocity blood flow produced by the reduced cross-sectional area of the inlet cannula 110, thereby minimizing or limiting tissue overgrowth on the pressure sensors 202. Additionally, in the illustrated embodiment, the pressure sensors 202 are located within the internal compartment 128 of the pump housing 104, and are secured to the pump housing 104. The pressure sensors 202 are therefore physically protected by the pump housing 104 and have a secure structural connection, which reduces or limits positional drift and mechanical stress variations on the pressure sensors 202.

Further, in the illustrated embodiment, the location of the pressure sensors 202 permits the pressure sensors 202 to be directly connected to the on-board controller 116 for receiving electrical power directly from the on-board controller 116, and for sending pressure measurement signals directly to the on-board controller 116. The direct connection between the pressure sensor 202 and on-board controller 116 simplifies the implant procedure by eliminating the need to run separate power or communication lines to the pressure sensor 202, and also improves performance of the blood pump 102 by reducing signal noise in pressure measurements, thereby providing more accurate pressure measurements.

The on-board controller 116 is operatively connected to the stator 112, and is configured to control operation of the pump 102 by controlling the supply of electrical current to the stator 112 and thereby control rotation of the rotor 114. Additionally, the on-board controller 116 is connected to the pressure sensors 202, and is configured to receive pressure measurements from the pressure sensors 202, determine or calculate cardiac events or characteristics based on the pressure measurements detected by the pressure sensors 202, and control operation of the pump 102 (e.g., rotation of the rotor 114) based on the pressure measurements detected by the pressure sensors 202 and/or the determined cardiac events or characteristics. In particular, the on-board controller 116 is configured to perform closed-loop speed control of the pump rotor 114 based on the pressure measurements received from the pressure sensors 202 and/or the determined cardiac events or characteristics. The on-board controller 116 can be configured to control the rotor 114 in continuous flow operation and/or pulsatile flow operation.

In some embodiments, for example, the on-board controller 116 is configured to control operation of the pump 102 to achieve a desired or preset pressure set point of blood in the left ventricle. The on-board controller 116 can periodically or continuously query the pressure sensors 202 to measure the pressure of blood flowing through the pump 102, and compare the detected pressure with the pressure set point. If the detected blood pressure is different from the pressure set point, the on-board controller 116 can adjust the speed of the rotor 114 (e.g., by controlling the supply of electrical current to the stator 112) to achieve the pressure set point. In some embodiments, the on-board controller 116 is configured to determine if the difference between the measured pressure and the pressure set point exceeds a threshold difference before adjusting the speed of the rotor 114.

The pressure set point can be established by user input, for example, from a patient or a clinician, and can be stored in a memory device of the on-board controller 116. The pressure set point can be a fixed (i.e., time invariable) pressure set point, or the pressure set point can be a time variable set point. For example, the pressure set point can vary according to different phases of the cardiac cycle. That is, the pressure set point can be defined by a pressure profile that defines a desired or target pressure set point at different times or phases of the cardiac cycle.

In some embodiments, the pressure set point is a minimum left ventricle pressure set point. That is, the on-board controller 116 adjusts the speed of the rotor 114 to achieve a minimum left ventricle pressure that is equal to the target pressure set point. The minimum left ventricle pressure is typically referred to as "filling pressure," and is one of the primary indicators of the body's demand for total cardiac output. In other embodiments, the pressure set point is based on an amplitude of the left ventricle pressure waveform (i.e., the difference between the maximum left ventricle pressure and the minimum left ventricle pressure). The amplitude of the left ventricle pressure waveform is affected by the contractility of the left ventricle, and is less susceptible to long term drift as compared to other pressure sensor-based measurements.

Further, in some embodiments, the pressure set point may be adjusted in real time based on pressure measurements received from the pressure sensors 202 and/or the determined cardiac events or characteristics. For example, in some embodiments, the on-board controller 116 is configured to increase or decrease the pressure set point based on the maximum slope of the measured ventricle pressure waveform (dP/dt). The maximum dP/dt is related to the contractility of the left ventricle, and can be used to adjust the pressure set point, and the resulting rotor speed, to achieve a desired left ventricle unloading. For example, the on-board controller 116 may be configured to increase the pressure set point and/or the rotor speed based on the determined maximum dP/dt to increase left ventricle unloading. Further, in some embodiments, the on-board controller 116 is configured to increase or decrease the pressure set point based on a determined heart rate of a patient. For example, an increased heart rate is indicative of increased need for cardiac output (e.g., from exercise), and the on-board controller 116 can be configured to increase the pressure set point by a corresponding amount. Additionally or alternatively, the on-board controller 116 may be configured to increase or decrease the pressure set point based on feedback received from an accelerometer included in the blood pump assembly 100. For example, the on-board controller 116 may determine that a user of the blood pump assembly 100 is exercising or engaged in rigorous activity based on feedback from an accelerometer, and increase the pressure set point or speed of the rotor accordingly.

Additionally, in some embodiments, the on-board controller 116 is configured to determine a target rotor speed based on a multi-variable algorithm or function that takes into account one or more of the measured pressure of the ventricle and the determined cardiac characteristics or events. In some embodiments, for example, the on-board controller 116 is configured to determine a target rotor speed based on a statistically weighted function with one or more of the following variables: heart rate, minimum ventricle pressure, ventricle pressure amplitude, and maximum dP/dt.

Additionally, in some embodiments, the on-board controller 116 is configured to control the speed of the rotor 114 according to a speed profile that defines a time-variable speed set point of the rotor 114. In such embodiments, the on-board controller 116 can be configured to modulate the speed of the rotor 114 to different speed set points within a single cardiac cycle of a patient's heart. This type of rotor speed control, also known as "synchronized pulsing", may be implemented by the on-board controller 116 in any suitable manner that enables the blood pump assembly 100 to function as described herein. In some embodiments, for example, the on-board controller 116 can be configured to increase the speed of the rotor 114 during systole (known as "co-pulsation"), or decrease the speed of the rotor 114 during systole (known as "counter-pulsation"). In yet other embodiments, the on-board controller 116 can be configured to increase the speed of the rotor 114 over a first period of time during systole, and decrease the speed of the rotor 114 over a second period of time during systole. Additionally, synchronized pulsing of the rotor may be implemented by the on-board controller 116 at varying intervals. For example, the on-board controller 116 can be configured to modulate the speed of the rotor 114 to different speed set points within a single cardiac cycle of a patient's heart, or across more than one cardiac cycle of a patient's heart (for example, across two cardiac cycles).

In other embodiments, the on-board controller 116 is configured to control the speed of the rotor 114 according to a fixed (i.e., time invariable) speed set point. In such embodiments, the on-board controller 116 can be configured to control the speed of the rotor 114 to achieve an average speed equal to the speed set point. Rotor speed profiles and/or set points can be established by user input, for example, from a patient or a clinician, and can be stored in a memory device of the on-board controller 116.

Figure 7:
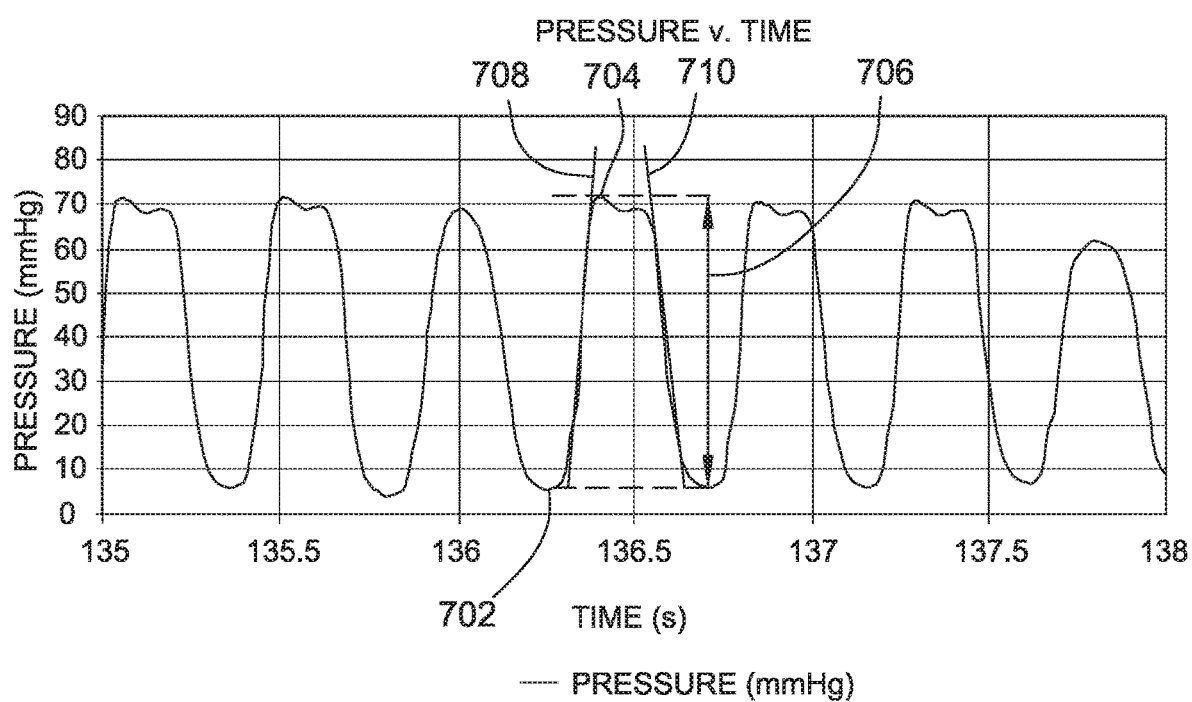
FIG. 7 is an example plot of data that may be collected and output by the sensor assembly of FIG. 6.

The on-board controller 116 can also be configured to calculate or determine physiological characteristics of a patient based on pressure data collected by the pressure sensors 202. FIG. 7 is an example plot of data that may be collected and output by the pressure sensors 202 during operation of the blood pump assembly 100. The example plot illustrates the left ventricle pressure waveform (i.e., pressure vs. time) over a period of about 3 seconds. Based on the data collected by the pressure sensors 202, the on-board controller 116 can calculate or determine various cardiac events or characteristics using known techniques and methods. In some embodiments, for example, the on-board controller 116 is configured to determine one or more of the following based on pressure data collected by the pressure sensors 202: heart rate, ventricular filling pressure or minimum pressure, maximum systolic pressure, pressure amplitude (i.e., the difference between maximum pressure and minimum pressure), average pressure, end systolic pressure, end diastolic pressure, atrial kick pressure, contractility (i.e., maximum systolic dP/dt), and relaxation (i.e., minimum systolic dP/dt). For example, the on-board controller 116 may be programmed to determine the heart rate of a patient by applying a fast Fourier transform to the pressure data collected by the pressure sensors 202, and/or by calculating a time interval between cardiac cycle detection points evident from the pressure waveform (e.g., beginning of systole, end of systole, beginning of diastole, and/or end of diastole).

The on-board controller 116 may also be programmed to determine ventricular filling pressure or minimum pressure, maximum pressure or maximum systolic pressure, pressure amplitude (i.e., the difference between maximum pressure and minimum pressure), average pressure, contractility (i.e., maximum systolic dP/dt), relaxation (i.e., minimum systolic dP/dt), end systolic pressure, end diastolic pressure, and atrial kick pressure by applying mathematical operations to the pressure data collected by the pressure sensors 202. For example, the on-board controller 116 may be configured to determine the ventricular filling pressure or minimum pressure by identifying a local minimum pressure value on the pressure waveform within a single phase of the cardiac cycle. An example ventricular filling pressure value is identified at point 702 in FIG. 7. Additionally, the on-board controller 116 may be configured to determine maximum systolic pressure by identifying a local maximum pressure value on the pressure waveform within a single phase of the cardiac cycle. An example maximum systolic pressure value is identified at point 704 in FIG. 7. The on-board controller 116 may be further configured to determine the pressure amplitude 706 within a single cardiac phase of the pressure waveform by determining the difference between the maximum pressure 704 and the minimum pressure 702. The on-board controller 116 may be further configured to determine contractility by determining the maximum slope 708 of the pressure waveform within the systolic phase of a single cardiac cycle. The on-board controller 116 may also be configured to determine relaxation by determining the minimum slope 710 of the pressure waveform within the systolic phase of a single cardiac cycle. The on-board controller 116 may also be configured to determine end-systolic pressure and end-diastolic pressure by identifying pressure values along the pressure waveform at the end of the systolic and diastolic phases, respectively, of the cardiac cycle. The on-board controller 116 may also be configured to identify atrial kick pressure by identifying the pressure value at a localized maximum value on the pressure waveform within the diastolic phase of a single cardiac cycle (i.e., between the end of systole of a first cardiac cycle, and the beginning of systole of a second cardiac cycle). The on-board controller 116 may be configured to determine or identify the various phases of the cardiac cycle (e.g., systole and diastole) for the pressure waveform based on, for example, minimum pressure values, maximum pressure values, maximum slope values, and minimum slope values. For example, the on-board controller 116 may be configured to determine that a certain portion of the pressure waveform corresponds to the systolic phase of the cardiac cycle by determining or identifying a region on the pressure waveform between the maximum slope and the minimum slope.

As noted above, one or more of the determined cardiac events or characteristics may be used by the on-board controller 116 to perform closed-loop speed control of the pump rotor 114. For example, an increase in heart rate, minimum ventricle pressure, or ventricle pressure amplitude generally indicates an increased need for cardiac output. Accordingly, in some embodiments, the on-board controller 116 is configured to adjust the speed of the rotor 114 by a corresponding amount when pressure data from pressure sensors 202 indicate an increase in heart rate, minimum ventricle pressure, and/or ventricle pressure amplitude.

Additionally, in some embodiments, one or more of the determined cardiac events or characteristics can be used to examine and/or evaluate physiologic cardiac function. For example, the left ventricle pressure amplitude (i.e., the difference between maximum pressure and minimum pressure) is a combined indicator of both filling pressure and heart contractility. The minimum dP/dt can be used to evaluate the relaxation speed of the ventricle and to identify possible fibrosis or electrical conduction issues. The maximum dP/dt can be used to evaluate the systolic elastance curve of the ventricle, which is a direct measure of left ventricle functional performance. This may be used, for example, to detect left ventricle recovery, and to adjust the target pressure and/or rotor speed set points stored in on-board controller 116 accordingly.

The on-board controller 116 can include one or more modules or devices that are enclosed within pump housing 104. The on-board controller 116 can generally include any suitable computer and/or other processing unit, including any suitable combination of computers, processing units and/or the like that may be communicatively coupled to one another (e.g., on-board controller 116 can form all or part of a controller network). Thus, on-board controller 116 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit (ASIC), a digital signal processor (DSP), a field programmable gate array (FPGA), and other programmable circuits. Additionally, the memory device(s) of on-board controller 116 may generally include memory element(s) including, but not limited to, non-transitory computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the on-board controller 116 to perform various functions including, but not limited to, controlling the supply of electrical current to the stator 112, determining the pressure and/or pressure waveform within the left ventricle of a patient's heart, determining or calculating cardiac events or characteristics based on the pressure measurements detected by the pressure sensors 202, such as heart rate, contractility, end-systolic pressure, end-diastolic pressure, atrial kick pressure, left ventricular contractility, max left ventricular pressure, and left ventricular relaxation, adjusting the speed of the rotor 114 based on the pressure detected by the pressure sensors 202 and/or one or more of the determined cardiac events or characteristics, outputting pressure measurement data to an external controller (e.g., external system controller 22), and various other suitable computer-implemented functions.

In the illustrated embodiment, the on-board controller 116 is implemented as one or more circuit boards 170 and various components carried on the circuit boards (e.g., processors and memory devices) to control operation of the pump 102 by controlling the electrical supply to the stator 112.

Figure 8:
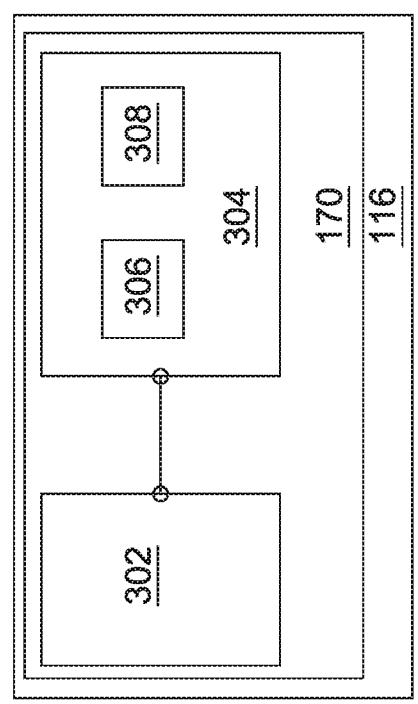
FIG. 8 is a schematic view of a controller included in the blood pump assembly of FIG. 4.

FIG. 8 is a schematic view of an embodiment of the on-board controller 116, which includes the circuit boards 170, one or more processors 302, and a memory device 304 operatively coupled to the one or more processors 302. The memory device 304 can include any suitable forms of memory, for example, a read only memory (ROM) 306 and a random access memory (RAM) 308. The ROM 306 can be used to store basic instructional sets for the operation of the one or more processors 302. The RAM 308, or any other suitable memory device such as long term, short term, volatile, nonvolatile, or other suitable storage medium, can be used to store patient specific parameters that are used by the on-board controller 116 to control patient specific operational aspects of the blood pump assembly 100, as well as related software modules.

A communication line (e.g., communication line 28) couples the blood pump assembly 100 and on-board controller 116 to the external system controller 22, which monitors system operation via various software applications. As noted above, the blood pump assembly 100 itself also includes several software applications that are executable by the on-board controller 116 for various functions, such as to control radial levitation and/or drive of the rotor 114 of the pump assembly 100 during operation. The external system controller 22 can in turn be coupled to batteries 24 or a power module (not shown) that connects to an AC electrical outlet. The external system controller 22 can also include an emergency backup battery (EBB) to power the system (e.g., when the batteries 24 are depleted) and a membrane overlay, including Bluetooth capabilities for wireless data communication. An external computer that is configurable by an operator, such as clinician or patient, can further be coupled to the circulatory support system 10 for configuring the external system controller 22, the implanted blood pump assembly 100, and/or patient specific parameters, updating software on the external system controller 22 and/or the implanted blood pump assembly 100, monitoring system operation, and/or as a conduit for system inputs or outputs.

Pressure data collected by pressure sensors 202 can be output to the external system controller 22 for additional processing. In some embodiments, for example, the external system controller 22 includes an atmospheric pressure sensor 32 (FIG. 1) for detecting an ambient pressure to facilitate determining a gauge pressure of blood flowing through the blood pump assembly 100. In such embodiments, the external system controller 22 can be configured to determine a gauge pressure of blood flow within the left ventricle of a patient's heart based on the pressure measurement data collected by the pressure sensors 202 and the ambient pressure data collected by the atmospheric pressure sensor 32. Additionally or alternatively, the on-board controller 116 can be configured to receive ambient pressure data from the external system controller 22, and determine a gauge pressure of blood flow within the left ventricle of a patient's heart. Further, the on-board controller 116 can be configured to control operation of the pump 102 (e.g., rotation of the rotor 114) based on the determined gauge pressure.

Figure 9:
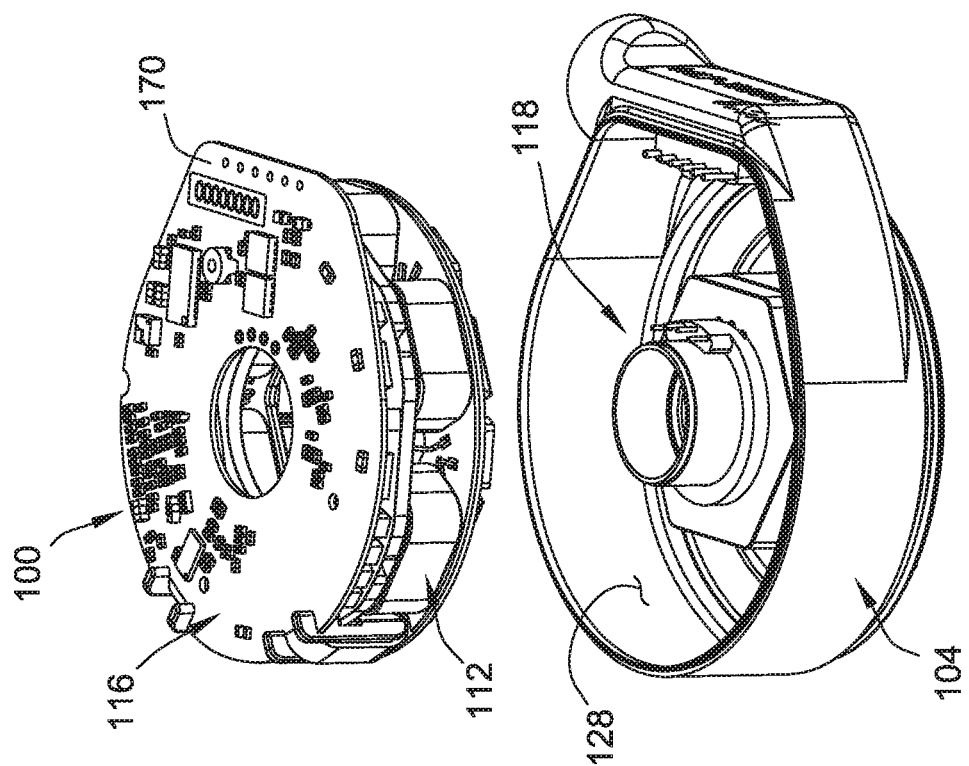
FIG. 9 is a partially exploded view of the blood pump assembly of FIG. 4.
Figure 10:
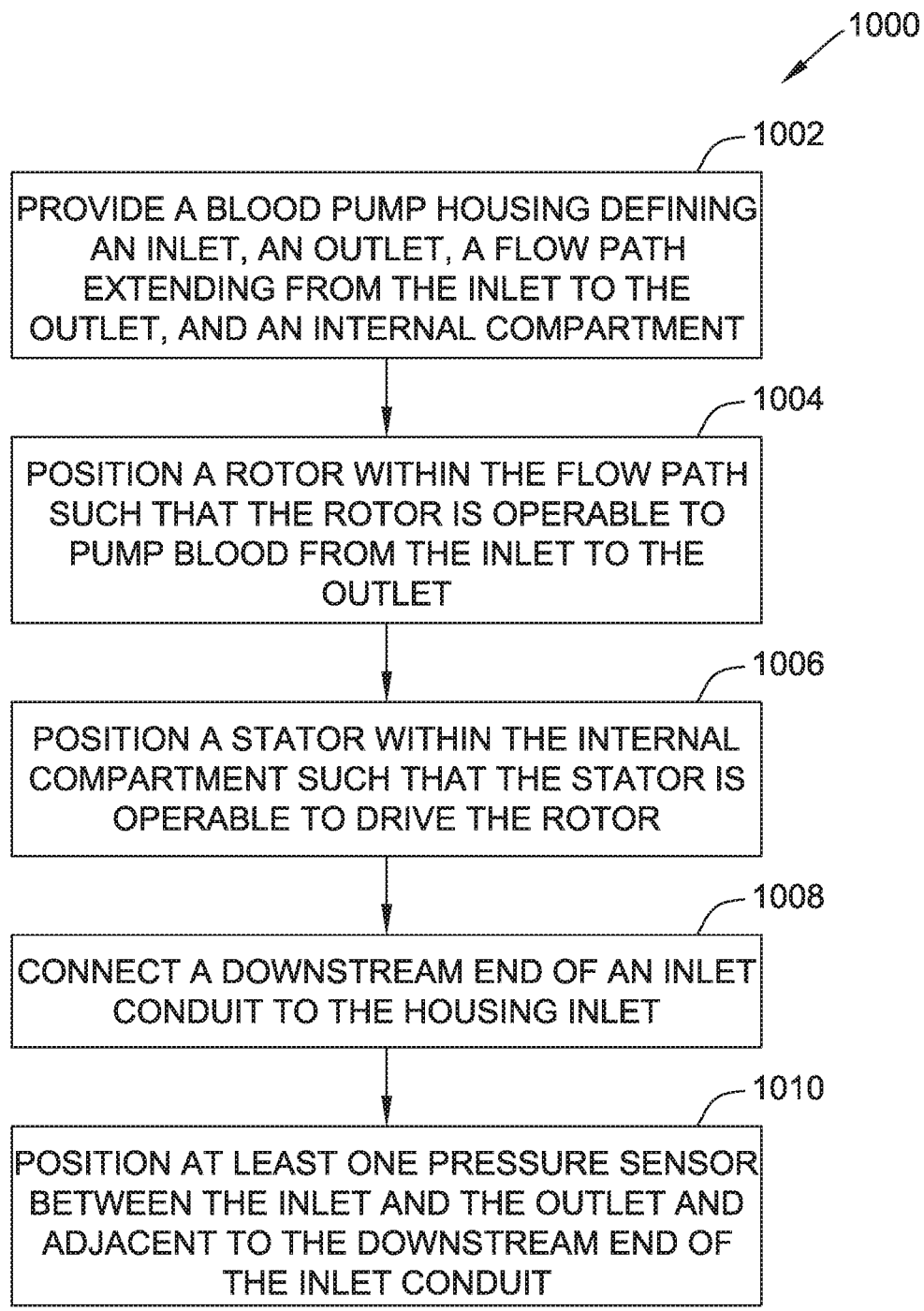
FIG. 10 is a flow diagram illustrating one embodiment of a method of assembling a blood pump assembly.

FIG. 9 is a partially exploded view of the blood pump assembly 100 shown in FIG. 4, and FIG. 10 is a flow diagram illustrating one embodiment of a method 1000 for assembling a blood pump assembly, such as the blood pump assembly 100 shown in FIG. 4. In the illustrated embodiment, the method 1000 includes providing 1002 a blood pump housing (e.g., blood pump housing 104) that defines an inlet, an outlet, a flow path extending from the inlet to the outlet, and an internal compartment separated from the flow path. The method 1000 further includes positioning 1004 a rotor (e.g., rotor 114) within the flow path such that the rotor is operable to pump blood from the inlet to the outlet, and positioning 1006 a stator (e.g., stator 112) within the internal compartment such that the stator is operable to drive the rotor. The method 1000 further includes connecting 1008 a downstream end of an inlet conduit (e.g., inlet cannula 110) to the housing inlet. The downstream end of the inlet conduit has a reduced cross-sectional area that produces a localized region of high velocity blood flow. The method 1000 further includes positioning 1010 at least one pressure sensor (e.g., pressure sensor 202) between the inlet and the outlet, and adjacent to the downstream end of the inlet conduit such that the at least one pressure sensor is configured to detect a pressure of blood flowing through the flow path.

In some embodiments, the step of positioning 1010 at least one pressure sensor within the internal compartment of the housing includes connecting a sensor assembly (e.g., pressure sensor assembly 118) to the housing, where the sensor assembly includes a housing, and the at least one pressure sensor is positioned within the sensor assembly housing. In such embodiments, the sensor assembly housing can include a sleeve that extends upstream from the sensor assembly housing, and the step of connecting 1008 a downstream end of an inlet conduit to the housing inlet includes positioning the downstream end of the inlet conduit within the sleeve.

In some embodiments, the method 1000 further includes positioning a controller (e.g., on-board controller 116) within the internal compartment, and connecting the controller to the at least one pressure sensor. In such embodiments, the controller can be configured to control a rotational speed of the rotor based on the pressure detected by the at least one pressure sensor. Further, in such embodiments, the method can further include directly connecting the at least one pressure sensor to the controller (e.g., via one or more pin connectors 220).

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

As described herein, the implantable blood pump assemblies of the present disclosure provide several advantages over previous VAD designs. For example, embodiments of the implantable blood pump assemblies disclosed herein include one or more pressure sensors located on or within a housing of the blood pump assembly and/or adjacent to or within a localized region of high velocity blood flow. By locating pressure sensors adjacent to or within a localized region of high velocity blood flow, tissue overgrowth on the pressure sensors is minimized or reduced. Additionally, pressure sensors that are located one or within the housing of a blood pump assembly can be physically protected by the pump housing and can be securely connected to the pump housing, which reduces or limits positional drift and mechanical stress variations on the pressure sensors. Further, pressure sensors that are located on or within the housing of a blood pump assembly can be directly connected to an on-board controller of the blood pump assembly for receiving electrical power directly from the controller and for sending pressure measurement signals directly to the controller. Such a direct connection between the pressure sensor and the controller simplifies the implant procedure by eliminating the need to run separate power or communication lines to the pressure sensor, and also improves performance of the blood pump by reducing signal noise in pressure measurements.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable blood pump assembly comprising:
a housing defining an inlet, an outlet, a rotor chamber, a flow path extending from the inlet to the outlet, and an internal compartment separated from the flow path;
a rotor positioned within the flow path and operable to pump blood from the inlet to the outlet;
a stator positioned within the internal compartment and operable to drive the rotor;
an inlet conduit connected to the housing inlet, the inlet conduit having a downstream end having a reduced cross-sectional area that produces a localized region of high velocity blood flow, the downstream end terminating at an outlet of the inlet conduit; and
at least one pressure sensor positioned between the housing inlet and the housing outlet and configured to detect a pressure of blood flowing through the flow path, wherein the at least one pressure sensor is located adjacent the downstream end of the inlet conduit, and between the outlet of the inlet conduit and the rotor chamber.

2. The implantable blood pump assembly of claim 1 further comprising a sensor assembly, the sensor assembly comprising the at least one pressure sensor and a housing, the at least one pressure sensor positioned within the sensor assembly housing.

3. The implantable blood pump assembly of claim 2, wherein the sensor assembly housing defines a sensor assembly flow path concentric with the downstream end of the inlet conduit, the sensor assembly housing further comprising a flexible membrane that transmits fluid pressure of blood flowing through the sensor assembly flow path to the at least one pressure sensor.

4. The implantable blood pump assembly of claim 2, wherein the sensor assembly housing comprises a sleeve that extends upstream from the sensor assembly housing, wherein the downstream end of the inlet conduit is positioned within the sleeve.

5. The implantable blood pump assembly of claim 2, wherein the at least one pressure sensor comprises a first pressure sensor and a second pressure sensor, wherein the first and second pressure sensors are positioned within the sensor assembly housing diametrically opposite one another.

6. The implantable blood pump assembly of claim 1, wherein the at least one pressure sensor is positioned within the internal compartment.

7. The implantable blood pump assembly of claim 1, wherein the at least one pressure sensor comprises a sensing element and a deflectable membrane positioned between the sensing element and the flow path.

8. The implantable blood pump assembly of claim 7, wherein the sensing element comprises at least one of a capacitive pressure sensing element or a piezo-resistive pressure sensing element.

9. The implantable blood pump assembly of claim 1 further comprising a controller connected to the at least one pressure sensor and the stator and positioned within the internal compartment, wherein the controller is configured to control a rotational speed of the rotor based on the pressure detected by the at least one pressure sensor.

10. The implantable blood pump assembly of claim 9, wherein the at least one pressure sensor is directly connected to the controller for receiving power therefrom and sending pressure measurement signals thereto.

11. The implantable blood pump assembly of claim 1, wherein the implantable blood pump assembly is configured as a centrifugal pump.

12. The implantable blood pump assembly of claim 1, wherein the rotor comprises a permanent magnet, and wherein the stator is operable to drive the rotor by generating an electromagnetic field that interacts with the permanent magnet of the rotor.

13. A circulatory support system comprising:
an implantable blood pump comprising:
a housing defining an inlet, an outlet, a rotor chamber, a flow path extending from the inlet to the outlet, and an internal compartment separated from the flow path;
a rotor positioned within the flow path and operable to pump blood from the inlet to the outlet;

a stator positioned within the internal compartment and operable to drive the rotor;

an inlet conduit connected to the housing inlet, the inlet conduit having a downstream end having a reduced cross-sectional area that produces a localized region of high velocity blood flow, the downstream end terminating at an outlet of the inlet conduit; and at least one pressure sensor positioned between the housing inlet and the housing outlet and configured to detect a pressure of blood flowing through the flow path, wherein the at least one pressure sensor is located adjacent the downstream end of the inlet conduit, and between the outlet of the inlet conduit and the rotor chamber; and a controller connected to the at least one pressure sensor and the stator and positioned within the internal compartment, wherein the controller is configured to control a rotational speed of the rotor based on the pressure detected by the at least one pressure sensor.

14. The circulatory support system of claim 13, wherein the at least one pressure sensor is directly connected to the controller for receiving power therefrom and sending pressure measurement signals thereto.

15. The circulatory support system of claim 13 further comprising an external system controller operatively connected to the blood pump for receiving pressure measurement data therefrom, wherein the external system controller comprises an atmospheric pressure sensor for detecting an ambient pressure, wherein the external system controller is configured to determine a gauge pressure based on the pressure measurement data and the ambient pressure.

16. A method of assembling a blood pump assembly, the method comprising:

providing a blood pump housing defining an inlet, an outlet, a rotor chamber, a flow path extending from the inlet to the outlet, and an internal compartment;

positioning a rotor within the flow path such that the rotor is operable to pump blood from the inlet to the outlet;

positioning a stator within the internal compartment such that the stator is operable to drive the rotor;

connecting a downstream end of an inlet conduit to the housing inlet, the downstream end having a reduced cross-sectional area that produces a localized region of high velocity blood flow, the downstream end terminating at an outlet of the inlet conduit; and positioning at least one pressure sensor between the housing inlet and the housing outlet, adjacent to the downstream end of the inlet conduit, and between the outlet of the inlet conduit and the rotor chamber such that the at least one pressure sensor is configured to detect a pressure of blood flowing through the flow path.

17. The method of claim 16, wherein positioning at least one pressure sensor between the inlet and the outlet includes connecting a sensor assembly to the blood pump housing, the sensor assembly including a housing, wherein the at least one pressure sensor is positioned within the sensor assembly housing.

18. The method of claim 17, wherein the sensor assembly housing includes a sleeve that extends upstream from the sensor assembly housing, wherein connecting a downstream end of an inlet conduit to the housing inlet includes positioning the downstream end of the inlet conduit within the sleeve.

\* \* \* \* \*